United States Patent [19]

Bharucha et al.

[11] 4,046,811

[45] Sept. 6, 1977

[54] ANTIVIRAL 1,2,3,4-TETRAHYDRO-1,4-ALKANONAPH-THALENAMINE DERIVATIVES

[75] Inventors: Kekhusroo R. Bharucha, Toronto; Djordje Ajdukovic, Montreal; Vytautas Pavilanis, Westmount; Angus Campbell Mackay, Toronto, all of Canada

[73] Assignee: Canada Packers Limited, Toronto, Canada

[21] Appl. No.: 578,871

[22] Filed: May 19, 1975

Related U.S. Application Data

[62] Division of Ser. No. 289,122, Sept. 14, 1972, Pat. No. 3,932,512.

[51] Int. Cl.$^2$ .............................................. C07C 87/64
[52] U.S. Cl. .................................. 260/578; 260/349; 260/453 AR; 260/501.1; 260/501.12; 260/514 G; 260/515 A; 260/546; 260/562 R; 260/566 A; 260/570.5 P; 260/570.8 R; 260/570.9; 260/576; 260/577; 260/586 R; 260/590 R; 424/316; 424/330

[58] Field of Search ........ 260/576, 577, 578, 570.8 R, 260/570.9; 424/330

[56] References Cited

FOREIGN PATENT DOCUMENTS 41-18944  1/1966  Japan .................................. 260/576

OTHER PUBLICATIONS

Kitahonoki et al., "Tetrahedron", vol. 24, pp. 4605-4623 (1968).
Tanida et al., "J. Org. Chem.", vol. 31 (12), pp. 3941-3947 (1966).

Primary Examiner—Daniel E. Wyman
Assistant Examiner—John J. Doll
Attorney, Agent, or Firm—Bacon & Thomas

[57] ABSTRACT

Amine derivatives of 1,2,3,4-tetrahydro-1,4-alkanonaphthalenes, and the use of such compounds to control viral infections, particularly influenza viruses, in warm-blooded animals are disclosed. Pharmaceutical compositions containing an effective amount of the novel compounds and a pharmaceutically acceptable carrier are also disclosed.

2 Claims, No Drawings

ANTIVIRAL 1,2,3,4-TETRAHYDRO-1,4-ALKANONAPHTHALENAMINE DERIVATIVES

This is a division of application Ser. No. 289,122, filed Sept. 14, 1973, now U.S. Pat. No. 3,932,512.

The present invention relates to 1,2,3,4-tetrahydro-1,4-methanonaphthalen-endo-2-amine and its pharmaceutically acceptable acid addition salts and to the production and use thereof.

It is an object of the present invention to provide new anti-viral agents, a process for preparing same and pharmaceutical compositions and methods for using them.

There are relatively few known compounds that have significant anti-viral activity against influenza viruses. One of these generally recognized as having prophylactic activity against these viruses is the hydrochloride of amantadine. Other compounds reported to have activity against influenza viruses are disclosed in U.S. Pat. Nos. 3,483,254, 3,496,228, 3,538,160, 3,534,084 and 3,592,934.

According to the invention, there have been discovered further compounds having pharmaceutical application and utility as anti-influenza agents. The compounds are characterized by low-toxicity combined with good activity against influenza viruses, particularly influenza virus $A_2$, as shown by standard tissue culture tests and by in vivo tests in mice.

It should be understood that the compound 1,2,3,4-tetrahydro-1,4-methanonaphthalen-endo-2-amine readily forms acid addition salts and such salts having a non-toxic anion are also included within the scope of the present invention.

Representative of such salts are the hydrochloride, hydrobromide, sulfate, phosphate, acetate, succinate, adipate, propionate, tartrate, citrate, bicarbonate, pamoate, cyclohexylsulfamate, and acetylsalicylate.

The general procedure for preparing 1,2,3,4-tetrahydro-1,4-methanonaphthalen-endo-2-amine is illustrated as follows:

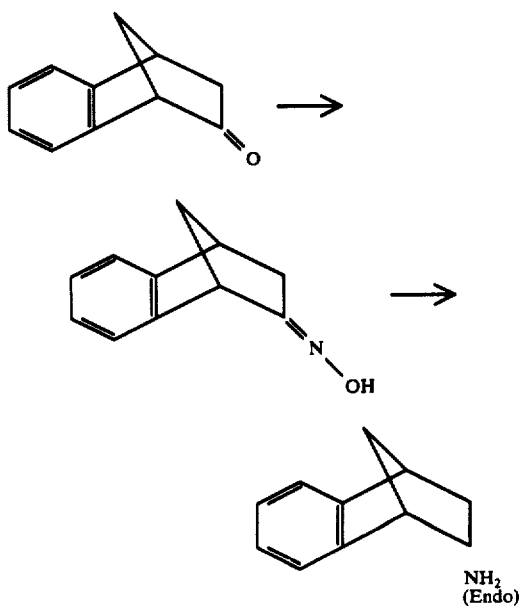

The starting material for the synthetic scheme outlined above is the benzonorbornen-2-one, which is produced by the reactions of benzonorbornadiene (1,4-dihydro-1,4-methanonaphthalene) with formic acid followed by oxidation of the oxo-2-formate with a solution of chromic acid. The preferential exo attack by the formic acid on the benzonorbornadiene is well established in these types of compounds.

The compound of structural formula I is prepared by reacting the ketone with hydroxylamine hydrochloride in the presence of sodium acetate. The oxime formed by the previous step is reduced with sodium metal in absolute ethanol to give the 1,2,3,4-tetrahydro-1,4-methanonaphthalen-endo-2-amine (I).

The invention will be further understood by reference to the following illustrative examples.

EXAMPLE 1

Preparation of 1,2,3,4-tetrahydro-1,4-methanonaphthalene-endo-2-amine (I).

Benzonorbornene-2-one [Cook et al, J. Org. Chem., 31, 14 (1966)] (1g.) was added to a solution of hydroxylamine hydrochloride (1.25g.) and sodium acetate (1.5g.) in water (5ml). Sufficient ethanol was then added to give a clear solution. This reaction mixture was heated on a water bath for 15 minutes and then shaken until a white solid (1.2g., 100%) precipitated. This material was filtered off and purified by crystallization from chloroform - light petroleum. The material was analyzed by infra-red, nuclear magnetic resonance and elemental analysis techniques and determined to be benzonorbornen-2-one oxime, $C_{11}H_{11}ON$ (m.p. 115°-116° C).

A solution of benzonorbornen-2-one oxime (2g.) in absolute ethanol (120ml) was heated to reflux under nitrogen the sodium metal (12 g.) was added in small portions with continuous stirring. The reaction mixture was then refluxed for 30 minutes. This viscous suspension was then cooled to room temperature, 100 ml. of water added and the reaction mixture agitated until a clear solution was obtained. This was extracted with ether and the ether extract worked up to give an oil which was dissolved in chloroform and extracted with 10% HCl solution. Removal of water and excess HCl under vacuum from this extract gave a white solid (1g., 40%). The white solid was analyzed by infra-red, nuclear magnetic resonance and elemental analysis techniques and was determined to be the 1,2,3,4-tetrahydro-1,4-methanonaphthalen-endo-2-amine hydrochloride, $C_{11}H_{14}NCl$ (m.p. 230°-231° C). Basification of a sample of this material with 10% NaOH gave, on ether extraction, the required amine as a pale yellow oil which was also analyzed by infra-red, and nuclear magnetic resonance techniques, and the empirical formula was determined to be $C_{11}H_{13}N$.

ANTIVIRAL ACTIVITY

A significant aspect of the instant invention resides in the discovery that benzonorbornene derivatives described having an amino substituent in the 2-endo configuration of the molecule exhibit enhanced activity as opposed to corresponding analogous compounds having other configurations.

As an example, the 1,2,3,4-tetrahydro-1,4-methanonaphthalen-endo-2-amine, one of the active antiviral compounds disclosed herein, when used in in vivo testing on mice infected with fatal influenza (influenza $A_2$) showed 66% survival in mice treated with this compound, whereas almost no survival was observed in the control group. However, the isomer with the amino substituent taking up the exo configuration showed no antiviral activity by in vitro test procedure.

In Vitro Activity of Anti-myxovirus Compounds

The in vitro activity of representative compounds of the present invention was determined as set forth below:

In preparing the compounds for testing, they were handled aseptically throughout. The compounds were dissolved in a minimum amount of a suitable solvent and the final dilutions were made up to the required volume in a complete culture medium used in assay and in concentration not exceeding the predetermined maximum non-toxic levels. All materials were tested first at three concentrations, and those which showed an inhibiting activity in that range were carefully retested at several concentrations below the maximum non-toxic levels.

The cell culture used in all primary in vitro anti-myxovirus assays was an established cell line of the human conjunctiva (G-2 cells). The cytotoxic studies of each of the compounds were performed prior to testing for antiviral activity to determine level of response of the cells to the potentially toxic action of the compounds. Cytotoxic levels were expressed as a minimal concentration which produces 50% degeneration of test cells ($CTD_{50}$) as compared to the appropriate controls, or as a maximal non-toxic concentration which does not produce any morphologically detectable degeneration of test cells ($CTD_o$).

Standard batches of virus were made by growing the virus in an appropriate cell culture, after passaging it on the chick embryo, and then making a pool which was dispersed in ampoules and kept frozen at $-76°$ C until used. The virus titer ($TCID_{50}$) was determined in the cell culture employed for the assays.

The cells were grown in test tubes in a suitable medium. Immediately before use the initial medium was replaced with the one containing the test compound in an appropriate concentration. After virus was added the infected culture was incubated at $32°$ C for a number of days. The medium was then drained, red blood cells added and after washing, the extent of hemadsorption evaluated. The percentage of inhibition of adsorption (a measure of antiviral activity) was then calculated.

In all anti-myxovirus testing in vitro, as well as in vivo, amantadine was used as a reference standard.

The results of in vitro tests compared to Amantadine are shown in the following tables:

| AMANTADINE HYDROCHLORIDE Influenza $A_2$/Aichi/3/68, G-2 cells: | | | |
|---|---|---|---|
| Cytotoxicity | Concentration | | |
| $CTD_{50}$  $CTD_0$ | of compounds | % Inhibition | |
| ($\mu$g/ml) | ($\mu$g/ml) | 100 $TCID_{50}$ | 56.2 $TCID_{50}$ |
| >100   >100 | 100 | 43 | 87 |
| | 90 | 67 | 97 |
| | 80 | 27 | 70 |
| | 70 | 33 | 83 |
| | 60 | 0 | 53 |
| | 50 | 0 | 0 |
| | 40 | 0 | 0 |
| | 30 | 0 | 0 |

| Influenza (swine), G-2 cells: | | | |
|---|---|---|---|
| Cytotoxicity | Concentration | | |
| $CTD_{50}$  $CTD_0$ | of compounds | % Inhibition | |
| ($\mu$g/ml) | ($\mu$g/ml) | 316 $TCID_{50}$ | 170 $TCID_{50}$ |
| >100   >100 | 100 | 100 | 100 |

-continued

| AMANTADINE HYDROCHLORIDE Influenza $A_2$/Aichi/3/68, G-2 cells: | | |
|---|---|---|
| 90 | 100 | 100 |
| 80 | 100 | 100 |
| 70 | 97 | 93 |
| 60 | 83 | 90 |
| 50 | 67 | 80 |
| 40 | 10 | 17 |
| 30 | 0 | 0 |

| 1,2,3,4-TETRAHYDRO-1,4-METHANONAPHTHALEN-ENDO-2-AMINE . HCl Influenza $A_2$/Aichi/3/68 (human), G-2 cells: | | | |
|---|---|---|---|
| Cytotoxicity | Concentration | | |
| $CTD_{50}$  $CTD_0$ | of compounds | % Inhibition | |
| ($\mu$g/ml) | ($\mu$g/ml) | 178 $TCID_{50}$ | 17.8 $TCID_{50}$ |
| >100   >100 | 100 | 90 | 97 |
| | 90 | 80 | 97 |
| | 80 | 77 | 97 |
| | 70 | 53 | 90 |
| | 60 | 37 | 87 |
| | 50 | 10 | 30 |
| | 40 | 0 | 13 |
| | 30 | 0 | 0 |

| Influenza (swine), G-2 cells: | | | |
|---|---|---|---|
| Cytotoxicity | Concentration | | |
| $CTD_{50}$  $CTD_0$ | of compounds | % Inhibition | |
| ($\mu$g/ml) | ($\mu$g/ml) | 316 $TCID_{50}$ | 178 $TCID_{50}$ |
| >100   >100 | 100 | 100 | 100 |
| | 90 | 97 | 100 |
| | 80 | 90 | 97 |
| | 70 | 70 | 93 |
| | 60 | 7 | 80 |
| | 50 | 0 | 7 |
| | 40 | 0 | 0 |

When the compounds of the instant invention are used as antiviral agents they may be employed alone or in combination with the usual pharmaceutically acceptable carriers which are discussed in detail in the aforementioned U.S. Pat. Nos. 3,483,254; 3,496,220; 3,538,160; 3,534,084; and 3,592,934. The proportion of the antiviral agent with respect to the carrier is determined by its solubility and chosen route of administration.

The antiviral compounds of this invention can be administered according to this invention by any means thst effects contact of the active ingredient compound with the site of influenza viral infection in the body of the living host. It will be understood that this includes the site prior to infection setting in as well as after. For example, administration can be intranasally, orally, or parenterally, that is subcutaneously, intravenously, intramuscularly, or intraperitoneally. Activity against influenza virus $A_2$ by the latter route has been confirmed by tests in mice.

The following Table shows the toxicity of compound I along with that of Amantadine.

| TOXICITY OF IN VITRO ACTIVE ANTI-MYXOVIRUS COMPOUNDS IN MICE | |
|---|---|
| Animals: | Charles River white mice, 9-11 g. of starting weight, 6 mice per group. |
| Amantadine and Compound I | |
| *I/P route: | 100-125-150-175-200 mg/kg (Compound I) 150-175-200,225,250, 275-300-325 mg/kg (Aman.) |
| **P/O route: | 200-225-250-275 (Compound I) Mice were weighed each day before administration of the drugs and doses adjusted according to the actual weight of individual animal. All drugs were dissolved in water and diluted to the proper concentration (e.g., 20% by |

| | | Maximal non-toxic dose $LD_0$ (mg/kg) | | 50% toxic dose $LD_{50}$ (mg/kg) | |
|---|---|---|---|---|---|
| Compounds | Route of Administration | Acute | Subacute | Acute | Subacute |
| Amatadine | I/P | 175 | 150 | 225 | 175–200 |
| Compound I | I/P | 125 | 100 | 100 | 100 |
| | P/O | 250 | 225 | 275 | 250–275 |

*I/P - intraperitoneally
**P/O - oral

In Vivo Activity of Anti-myxovirus Compounds

In our experimental models for testing of anti-myxovirus activity mice were intranasally infected with mouse adapted human influenza $A_2$ virus in an amount to cause development of acute influenza resulting in death of animals. When animals so infected were treated with Amantadine (the reference "positive control" substance) or Compound I administered intraperitoneally, those compounds exhibited a significant antiviral effect against influenza virus infection. The results of some of these tests are summarized in the following table:

| Expt. | virus Dose ($LD_{50}$) | Drug | Drug Dose (I/P, mg/kg) | Survival S/T** | % | Mean Survival Time* Days | Increase (Days) |
|---|---|---|---|---|---|---|---|
| 1 | 1.44 | Virus, only | 0 | 10/30 | 33.3 | 8.07 | 0 |
| | | Amantadine | 80 | 27/30 | 90.0 | 15.4 | 7.33 |
| | | Compound I | 80 | 26/30 | 86.7 | 15.4 | 7.33 |
| 2 | 2.24 | Virus, only | 0 | 4/27 | 14.8 | 12.2 | 0 |
| | | Amantadine | 100 | 26.27 | 96.3 | 14.9 | 2.7 |
| 3 | 2.88 | Virus, only | 0 | 1/24 | 4.2 | 10.1 | 0 |
| | | Amantadine | 100 | 11/12 | 91.6 | 14.6 | 4.5 |
| | | Compound I | 100 | 8/12 | 66.4 | 13.8 | 3.1 |

*Mean survival time (days) = number of mice alive each day (up to the last day of experiment) divided by total number of mice in group.
**T = Total number of animals infected
S = Number of surviving animals These results indicate that the treatment of influenza $A_2$ infection in mice with the compounds of the invention produces a reduction in mortality under the experimental conditions chosen. They compare favorably with Amantadine which is one of the few compounds presently known which is generally accepted to be significantly active against influenza in vivo.

In the following experiment, compound I was tested at different levels for preventive control of influenza as follows:

Animals: Charles River white mice, starting weight: 10-12 g; 12 mice per group (24 mice as control).

Virus: Mice were inoculated intranasally with influenza $A_2$ virus Aichi/2/68, with a titer of 2,88 $LD_{50}$, suspended in PBS.

Compound I: Mice were divided into 5 groups and received respective doses of the drug: 100-85-70-55-40 mg/kg/day intraperitoneally, once a day for 16 days beginning one day prior to infection with the virus. Mice were weighed each day before inoculations and doses adjusted according to the actual weight of each animal. The active compound was suspended in phosphate buffered saline.

The results are shown in the following tables:

| | | DAYS POSTINFECTION / CUMULATIVE MORTALITY | | | | | | |
|---|---|---|---|---|---|---|---|---|
| | GROUP | 8 N/% | 9 N/% | 10 N/% | 11 N/% | 12 N/% | 13 N/% | 14 N/% |
| | Control (virus only) | 2/8.3 | 11/45.8 | 17/70.8 | 21/87.5 | 21/87.5 | 23/95.8 | 23/95.8 |
| COMPOUND I + virus | 100mg/kg | 0/0 | 0/0 | 2/16.7 | 3/25.0 | 4/33.3 | 4/33.3 | 4/33.3 |
| | 85 mg/kg | 0/0 | 1/8.3 | 3/25.0 | 4/33.3 | 6/50.0 | 6/50.0 | 6/50.0 |
| | 70mg/kg | 1/8.3 | 5/41.7 | 6/50.0 | 6/50.0 | 6/50.0 | 6/50.0 | |
| | 55mg/kg | 1/8.3 | 2/16.7 | 5/41.7 | 7/58.3 | 9/75.0 | 11/91.6 | 11/91.6 |
| | 40mg/kg | 1/8.3 | 5/41.7 | 7/58.3 | 9/75.0 | 10/83.3 | 11/91.6 | 11/91.6 |

From the foregoing it will be seen that the maximum single dosage for compound I should be no greater than 100 mg/kg.

| | | Survivors | | | Mean survival time | |
|---|---|---|---|---|---|---|
| Group (dose) | | $S/T^{(a)}$ | % | $p^{(b)}$ | Days | Increase (days) |
| Virus control (2.9 $LD_{50}$) | | 1/24 | 4.2 | — | 10.1 | 0 |
| Virus - CPD I (100mg/kg) | | 8/12 | 66.4 | 0.01 | 13.6 | 3.5 |
| Virus - CPD I ( 85 mg/kg) | | 6/12 | 30.0 | 0.01 | 12.9 | 2.0 |
| Virus - CPD I ( 70mg/kg) | | 6/12 | 50.0 | 0.01 | 12.4 | 2.3 |
| Virus - CPD I ( 55mg/kg) | | 1/12 | 9.3 | | 11.2 | 1.1 |
| Virus - CPD I ( 40mg/kg) | | 1/12 | 8.3 | | 10.5 | 0.4 |

$^{(a)}$Total number of animals infected
$^{(b)}$Probability factor - less than 0.3 significant antiviral activity, less than 0.05 highly significant antiviral activity.

Similar results have been demonstrated with other compounds of the invention.

The compounds within the scope of this invention are valuable for influenza viral prophylaxis, as well as for therapeutic treatment.

In general, the compounds of this invention are most desirably administered at a concentration level that will afford effective results without causing any harmful or deleterious side effect in the subject being treated, i.e., in an effective, non-toxic amount. The dosage administered will also be dependent upon the virus being treated, the age, health and weight of the recipient, the extent of infection, kind of concurrent treatment if any, frequency of treatment, and the nature of the effect desired. For example, a daily dosage of 10 to 100 mg/kg of body weight of compound I dissolved or suspended in phosphate buffer solution (PBS) may be safely and effectively administered to mice by the intraperitoneal route. Dosages are readily adjusted by known procedures for administration to other animal hosts including human and avian hosts.

The compounds of the present invention can be employed in dosage form in combination with pharmaceutically acceptable carriers, solvents, diluents and the like to provide liquid solutions or suspensions for intranasal or parenteral use.

In general, water, saline, aqueous dextrose (glucose) and related sugar solutions and glycols such as propylene glycol or polyethylene glycol are preferred liquid carriers, particularly for injectable solutions. Sterile injectable solutions such as buffered saline will ordinarily contain from about 0.5% to 25% by weight of the active ingredient.

It will be apparent from the foregoing descriptions that the 1,2,3,4-tetrahydro-1,4-alkanonaphthalenamine product of this invention and its acid salt derivatives constitute a valuable class of antiviral agents. One skilled in the art will also appreciate that the processes disclosed in the above examples are merely illustrative and are capable of wide variation and modification without departing from the spirit of this invention.

We claim:

1. A compound selected from the group consisting of 1,2,3,4-tetrahydro-1,4-methanonaphthalen-endo-2-amine and its pharmaceutically acceptable acid addition salts.

2. The hydrochloride salt of the compound named in claim 1.

* * * * *